United States Patent [19]

Speidel

[11] 4,243,201
[45] Jan. 6, 1981

[54] DEFLATION VALVE FOR BLOOD PRESSURE MEASURING DEVICE

[76] Inventor: Blasius Speidel, Hochmeisterstrasse 33, 7455 Jungingen, Fed. Rep. of Germany

[21] Appl. No.: 850,730

[22] Filed: Nov. 11, 1977

[30] Foreign Application Priority Data

Nov. 11, 1976 [DE] Fed. Rep. of Germany ....... 2651553

[51] Int. Cl.³ .............................................. F16K 31/00
[52] U.S. Cl. .................................... 251/297; 128/685; 128/274
[58] Field of Search ........................... 251/89, 90, 297; 128/2.05 A, 2.05 C, 2.05 G, 2.05 M, 274, 685

[56] References Cited

U.S. PATENT DOCUMENTS

| 2,616,658 | 11/1952 | Dombeck | 251/297 |
| 2,975,805 | 3/1961 | Horn | 251/297 |
| 3,738,357 | 6/1973 | Hayes | 251/285 |
| 4,013,265 | 3/1977 | Speidel | 251/205 |
| 4,029,295 | 6/1977 | Wassmer | 251/297 |

FOREIGN PATENT DOCUMENTS

| 75490 | 10/1947 | Austria | 251/297 |
| 2338596 | 2/1975 | Fed. Rep. of Germany . | |
| 2429046 | 1/1976 | Fed. Rep. of Germany . | |
| 2651553 | 8/1978 | Fed. Rep. of Germany | 128/685 |
| 2747060 | 4/1979 | Fed. Rep. of Germany | 128/685 |
| 1106037 | 12/1955 | France | 251/297 |

Primary Examiner—William R. Cline
Assistant Examiner—H. Jay Spiegel
Attorney, Agent, or Firm—Joseph A. Geiger

[57] ABSTRACT

A dual-function deflation valve for hand-held blood pressure measuring devices with a finger-depressible valve actuating lever which has a detent mechanism capable of retaining the lever in the fully open valve position, for a quick release of residual air pressure from the measuring cuff. The detent mechanism has two detent members with cooperating cam formations defined by the valve housing and valve actuating lever, respectively, either on coextending wall portions of both, or on a wall portion of the actuating lever and on a spring member which is mounted in a recess of the housing.

6 Claims, 8 Drawing Figures

DEFLATION VALVE FOR BLOOD PRESSURE MEASURING DEVICE

BACKGROUND OF THE INVENTION

1. Field of the Invention

The present invention relates to blood pressure measuring devices, or sphygmomanometers, and, more particularly, to an adjustable deflation valve for a manually inflatable and deflatable blood pressure measuring device.

The measuring of a person's blood pressure, using the auskultatory method of Riva-Rocci, involves the placement of an inflatable measuring cuff around the person's limb and the reading of the cuff pressure at the occurrence of two characteristic changes in the noise which is produced by the arterial blood flow. The established measuring procedure requires the measuring cuff to a pressure under which the blood flow is surpressed and by then slowly reducing the pressure until a first change in noise signals the so-called systolic pressure and, after a further slow reduction of the pressure, a second change in noise signals the so-called diastolic blood pressure level. The two pressure levels having been ascertained, the blood pressure measuring device needs to be completely deflated, before the measuring cuff can be removed from the person's limb.

It has been found that, when using an ordinary deflation valve which is sensitive enough to produce acceptable blood pressure readings, the final deflation of the device takes an inordinate amount of time, as the rate at which air flows out of the measuring cuff decreases exponentially with decreasing pressure.

It has therefore already been suggested that blood pressure measuring devices should be equipped with a deflation valve that has a "dumping" capability, meaning that, while regular actuation of the valve produces the desired slow deflation of the measuring sleeve, a special manipulation of release of the air from the measuring cuff. Advantageously, the deflation valve has a detent capability in its dumping mode, so that the operator need not further attend to the complete evacuation of the air from the measuring cuff, but can perform another task during this time, such as, for example, the recording of the measurements obtained.

Special dual-function valves for this purpose have already been suggested in the past. One such valve is disclosed in my U.S. Pat. No. 4,013,265 which suggests a deflation valve with a pivotably depressible actuating lever which, over a first movement range produces a slow, controlled pressure release and, over a second movement range in the same direction, opens dumping passages in the valve mechanisms. This prior art valve consists essentially of a valve housing with an axial main bore linking the pressure source—an inflation bulb, for instance—to the measuring cuff and pressure gauge. A cross bore in the valve housing leads transversely away from the main bore, in the direction of a pivotable actuating lever. The exit port of this cross bore is a slightly tapered, almost cylindrical valve seat. A matchingly tapered elongated valve plunger extends both ways through this valve seat, the outer extremity of the plunger being engaged by a pivotable actuating lever which, when depressed, pushes the valve plunger into the valve housing, against a spring, thereby opening an annular exit channel around the plunger. The dumping capability is achieved by providing grooves or slots in the valve plunger which, in the normal movement range of the actuating lever, remain outside the range of the valve seat and which, in the dumping position of the actuating lever, provide a greatly increased exit channel across the valve seat.

This prior art deflation valve also suggests a detent mechanism which is capable of retaining the actuating lever in the dumping mode. This detent mechanism may include an upstanding detent member, in the form of either an integral tongue portion of the valve housing or a special leaf spring attached to the valve housing, with a detent extremity which is movable in a radial sense with respect to the pivot axis of the actuating lever. An integral nose portion of the actuating lever, or a detent pin mounted in the lever, moves against the detent extremity of the detent member, as the actuating lever is pivoted about its axis, into its dumping position. The valve may also include a special counter-spring which, by suddenly increasing the movement-opposing bias on the actuating lever, prevents the accidental shift from the normal slow-deflation mode of the valve to the dumping mode.

Another prior art deflation valve with dumping capabilities is disclosed in U.S. Pat. No. 3,738,357. This valve features a valve housing with an axial main bore and a transverse cross bore accommodating a poppet valve controlling an exit port. The poppet valve is operated by means of a depressible actuating cap whose opening displacement is adjustably limited by means of a resettable stop cam, thereby exactly determining the rate of air release during the normal deflation mode. A rotation of the actuating cap about its axis brings the latter out of reach of the stop cam, so that the actuating cap can be further depressed, for the establishment of a dumping mode. In the fully depressed position, the actuating cap jams against the flank of the stop cam, thereby holding this position until the cap is forcibly retracted.

The known prior art deflation valves with dual-mode capability have various shortcomings. In some instances, there have been encountered problems of production tolerances and assembly difficulties, coupled with increased fabrication costs. Other versions are prone to operating problems, especially in connection with the detent mechanism or the jamming and unjamming of the valve actuating member in the dumping mode.

SUMMARY OF THE INVENTION

Underlying the present invention is the primary objective of providing an improved deflation valve, especially designed for use with blood pressure measuring devices, which has a slow-deflation mode for the controlled release of air from the measuring cuff, and a dumping mode for the rapid release of the residual air pressure from the measuring cuff. Once depressed to the dumping mode, the actuating lever of the deflation valve is to remain in this position, without finger pressure, until it is forcibly returned to the closed position. This feature is to be achieved by means of an improved detent mechanism which is simple in structure and reliable in operation.

The present invention proposes to attain this objective by suggesting a deflation valve adapted for use in a blood pressure measuring device and including, as known features, a valve housing with a main bore which communicates with the pressurizable measuring cuff of the device, an outlet bore leading from the main bore to the atmosphere and having a bore portion which serves as a valve seat, a valve plunger which is movable axially in the outlet bore and which cooperates with the valve seat so as to progressively open and close the outlet bore, an actuating lever pivotably mounted on the valve housing and operatively connected to the valve plunger to effect an opening movement of the valve plunger, when the lever is depressed towards the housing, and a plunger return spring exerting a bias in opposition to said opening movement; the deflation valve further including, as novel features, detent means for releasably retaining the actuating lever in a depressed position, against the bias of the return spring, said detent means including two cooperating detent members associated with the actuating lever and the valve housing, respectively, whereby at least one of the two detent members is part of a wall portion with an exposed detent face which coincides substantially with a surface portion of a body of rotation with reference to the pivot axis of the actuating lever, and at least one of the two detent members is resiliently deformable in a direction transverse to said detent face. The two detent members have cooperating detent cam formations in the form of a protrusion of one member and a matching depression of the other member, arranged in said exposed detent face, the detent cam formations being so located on the actuating lever and valve housing, respectively, that they engage each other, under deformation of the resiliently deformable member, when the actuating lever approaches its fully depressed position.

In a preferred embodiment of the invention, the exposed detent face is a part of the valve housing, the latter having oppositely facing parallel side walls oriented perpendicularly to the pivot axis of the actuating lever. The actuating lever itself has a U-shaped cross section, defined by a central bridge portion and oppositely adjoining side wall portions which extend parallel to the side walls of the valve housing, on the outside thereof, thereby serving as the second detent member, in cooperation with the housing side walls. The particular shape of the actuating lever allows for the side wall portions to flex outwardly, away from the housing side walls, thus providing said resilient deformability. While it is possible to arrange the cooperating depressions and protrusions of the suggested detent cam formations in either the side walls of the valve housing or the side wall portions of the actuating lever, it is preferable to arrange the depressions on the valve housing and the protrusions on the actuating lever. These formations are preferably matching detent grooves and detent ridges which are oriented radially with respect to the pivot axis of the actuating lever. The cooperating detent ridges and detent grooves have preferably a triangular cross section.

The arrangement of the detent cam formations on parallel wall portions of the valve housing and of the actuating lever greatly simplifies the structural shapes of the two parts, for easier mass production as injection-molded parts. The fact that the detent grooves and detent ridges are at all times covered by the side wall portions of the actuating lever increases the longevity of the valve, as accidental damage to one or both detent members is prevented. The arrangement of identical detent members on both sides of the valve further improves its operational reliability, by stabilizing the movement of the actuating lever and by neutralizing any clearance of the actuating lever on its pivot pin.

In another embodiment of the invention, the actuating lever is recessed into the valve housing, having a generally triangular outline. Because of this outline, the detent mechanism is arranged on only one side wall of the actuating lever, a flexible spring member being mounted inside the valve housing so as to cooperate with a detent groove on the lever sidewall. The oblique-faced valve housing, serving as a mounting support for the pressure gauge, makes it possible to arrange the pressure gauge, deflation valve, and inflation bulb in a compact hand-held assembly. The spring detent member is preferably a cantilever-type spring of round or flat stock, its attached end portion being held between the oblique mounting face of the valve housing and the bottom of the pressure gauge, may be provided to counteract the pressure of the spring member against the lever side wall.

The proposed embodiments of the improved deflation valve are of very simple, yet robust construction, thus being economical in production, while giving reliable service over the long run.

BRIEF DESCRIPTION OF THE DRAWINGS

Further special features and advantages of the invention will become apparent from the description following below, when taken together with the accompanying drawings which illustrate, by way of examples, several embodiments of the invention, represented in the various figures as follows.

DESCRIPTION OF THE PREFERRED EMBODIMENTS

Figure 1:
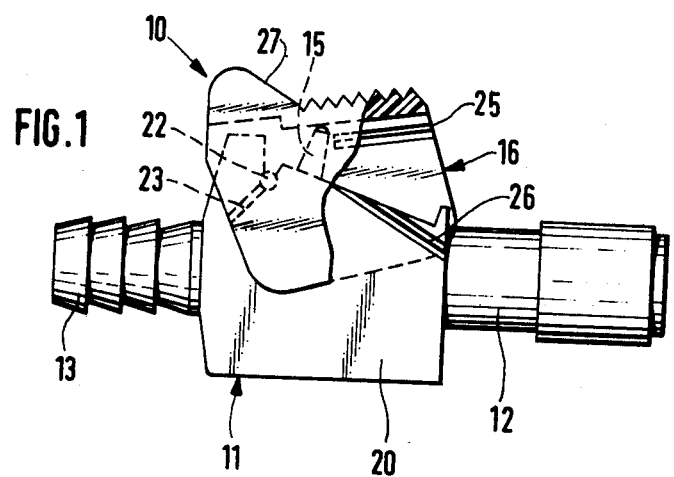
FIG. 1 is an elevational view, partially cross-sectioned, of a deflation valve embodying the present invention.
Figure 2:
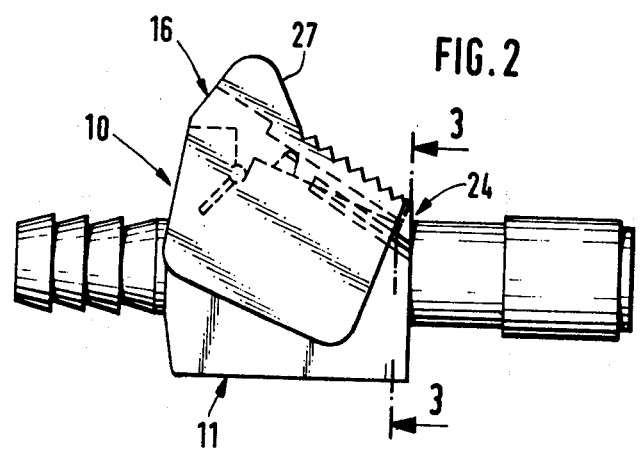
FIG. 2 shows the deflation valve of FIG. 1 in the fully open or "dumping" position.
Figure 3:
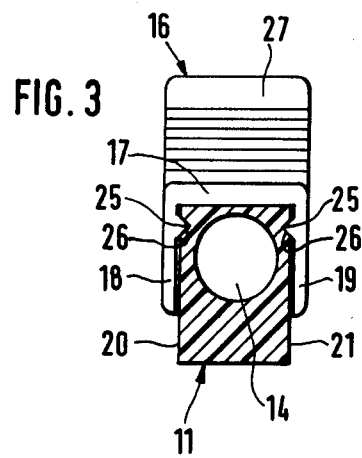
FIG. 3 shows a transverse cross section through the deflation valve of FIGS. 1 and 2, taken along line 3—3 of FIG. 2.

Referring to the accompanying drawings, and, more particularly, to FIGS. 1-3, it can be seen that the present invention represents an outgrowth of my prior invention, described in U.S. Pat. No. 4,013,265, the disclosure of which is to be considered incorporated in this disclosure.

In FIGS. 1-3 is shown a deflation valve 10 for a blood pressure measuring device. This valve consists essentially of a valve housing 11 with an axial main bore 14 (FIG. 3) leading through the housing and through a forwardly extending connecting nipple 13 and a rearwardly extending connecting tube 12. To the former is normally attached a flexible air hose whose other end is connected to the measuring cuff of the device (not shown), to the latter is attached an inflation bulb (likewise not shown). Inside the valve housing 11, in line with the valve plunger 15, of which only the upper portion is shown, is further arranged a cross bore which leads from the main bore 14 to a tapered valve seat surrounding the valve plunger on the upper side of the housing 11. Inside the cross bore is further arranged a plunger return spring which urges the valve plunger 15 outwardly, into a closed position against the valve seat. The cross bore, valve seat, valve plunger, and plunger return spring may be part of a subassembly which is mounted inside a removable valve insert.

The valve plunger 15 controls an air outlet through which the pressure in the measuring cuff can be gradually reduced, as required for the determination of the two blood pressure values. The complete depression of the valve plunger 15 opens up additional air passages, for the rapid release or "dumping" of the residual air pressure from the measuring cuff.

The opening position of the valve plunger 15 is controlled by means of an actuating lever 16 which is pivotably attached to the valve housing 11 by means of a pivot pin 22. The latter is an integral part of the actuating lever 16, being snappable into a suitable pin lodgement of the valve housing 11, as a result of a clamping slot 23 which renders a portion of the valve housing flexible.

The actuating lever 16 has the shape of an inverted "U", with side wall portion 18 and 19 reaching over the parallel side walls 20 and 21 of the valve housing 11. A linking bridge portion 17 of lever 16 is designed for finger application, having on its outside appropriate anti-slip ridges and a hump with a release flank 27, the purpose of which will be described further below. The inner side of the bridge portion 17 engages the upper extremity of the valve plunger 15. Thus, when the actuating lever 16 is gradually depressed, it slowly pushes the valve plunger 15 into the valve housing 11, away from its valve seat. The fully closed and fully open positions of the actuating lever 16 and of the valve plunger 15 are shown in FIG. 1 and FIG. 2, respectively.

As can be seen in FIG. 3, the valve housing 11 has a generally rectangular cross section, its side walls 20 and 21 serving to loosely guide the overhanging side wall portions 18 and 19 of the actuating lever 16. The four walls are thus perpendicular to the pivot axis of the actuating lever 16.

The deflation valve 10 is normally self-closing, under the influence of its plunger return spring (not shown), meaning that finger pressure is necessary to maintain the actuating lever 16 in the desired deflation position. A removal of the finger pressure will immediately close the valve. However, for a complete evacuation of the measuring system, following termination of the measuring procedure, the deflation valve 10 also has a detent mechanism 24 which maintains the valve in its dumping mode, i.e. the fully open valve position, without requiring finger pressure on the actuating lever 16. For this purpose, the housing side walls 20 and 21 and the lever side wall portions 18 and 19 have cooperating detent members in the form of triangular detent grooves 26 in the housing side walls 20 and 21 and matching triangular detent ridges 25 in the lever side wall portions 18 and 19. The detent grooves 26 and cooperating detent ridges 25 are preferably arranged in a near-radial orientation with respect to the pivot axis of the actuating lever, although this is not a requirement.

In order to obtain a highly sensitive adjustment operation on the actuating lever 16 and valve plunger 15, it is desirable to minimize the frictional contact between the valve housing 11 and the actuating lever 16. This can be achieved by arranging the location of the detent members 25 and 26 near the upper edge of the valve housing 11 and close to the bridge portion 17 of the actuating lever 16, so that the protruding detent ridges 26 will not come in contact with the housing side walls 20 and 21, until the actuating lever 16 has almost reached its dumping end position. Alternatively, if the detent ridges were to be arranged on the valve housing 11, with cooperating detent grooves in the side wall portions 18 and 19 of the actuating lever 16, then it would be preferable to locate these grooves near the lower edges of the lever side wall portions 18 and 19.

The flexibility of the side wall portions 18 and 19 and bridge portion 17 of the actuating lever 16, in conjunction with the particular shape and depth of engagement of the detent cam formation has to be such that the pivoting torque required for the disengagement of the detent ridges 25 from the detent grooves 26 is greater than the torque which is exerted against the actuating lever 16 by the fully depressed plunger return spring. Accordingly, while the detent mechanism 24 retains the actuating lever 16 in the dumping position (FIG. 2), it can readily be released from this position by applying finger pressure against the inclined release flank 27, thereby creating a counterclockwise torque on the actuating lever 16 which adds itself to the valve closing torque produced by the plunger return spring. This deflation valve is thus designed for operation with one finger, preferably the thumb of the hand in which the unit is held.

Figure 4:
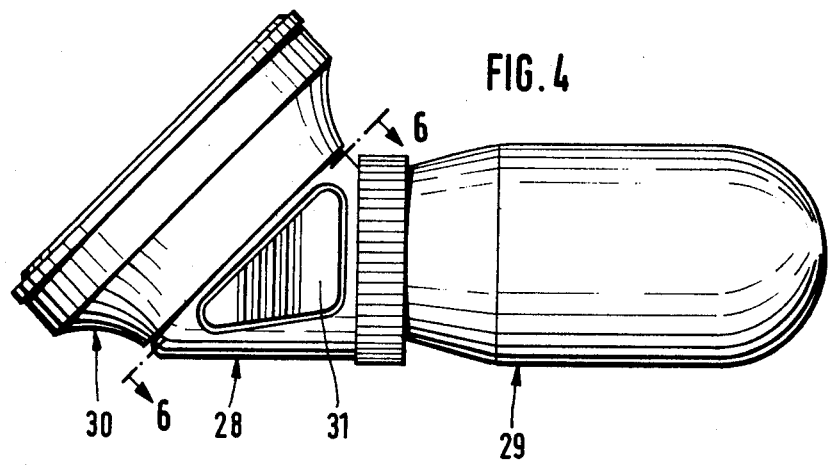
FIG. 4 is an elevational view of a compact pressure unit of a blood pressure measuring device, with a deflation valve representing a second embodiment of the invention serving as the central element of the unit.
Figure 5:
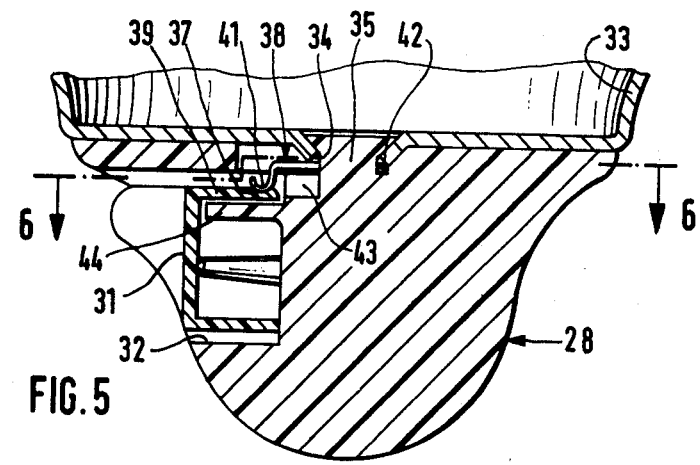
FIG. 5 shows a transverse cross section through the deflation valve of FIG. 4, taken along line 5—5 of FIG. 6.
Figure 6:
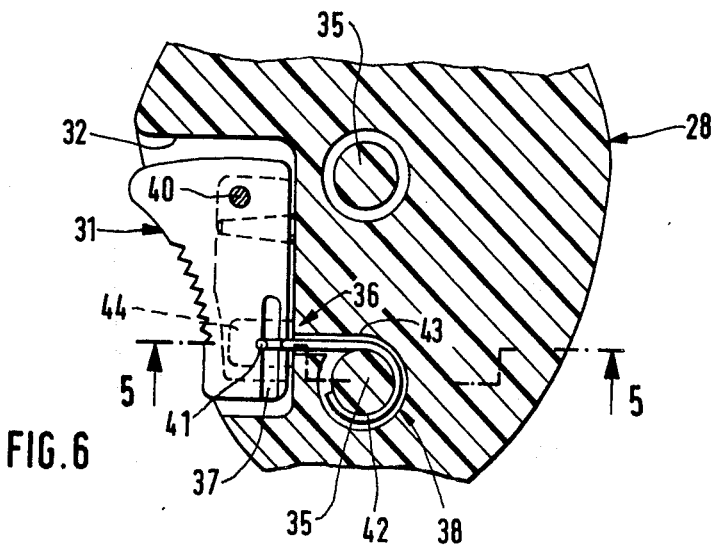
FIG. 6 shows a longitudinal cross section through the deflation valve of FIG. 4, taken along line 6—6 of FIGS. 4 and 5.

In FIGS. 4–6 is shown a second embodiment of the invention, as applied to a compact blood pressure measuring device which has a valve housing 28, a pressure gauge 30, and an inflation bulb 29 mounted together in a hand-held pressure unit. The valve housing 28 has an oblique mounting face for the pressure gauge 30, thus giving the housing 28 a generally triangular contour. As is shown in FIG. 4, the actuating lever 31 has a corresponding triangular contour, being recessed into the body of the valve housing 28. This is shown in detail in FIGS. 5 and 6. The valve housing 28 of this embodiment has a rounded lower contour, being preferably injection-molded of plastic material. FIG. 5 shows how the cup-shaped sheet metal housing 33 of the pressure gauge 30 is directly attached to the oblique mounting face of the valve housing 28. For this purpose, the gauge housing 33 has two openings 34 surrounded by outwardly tapering wall portions into which are engaged matching weld buttons 35 of the valve housing 28. These weld buttons, initially cylindrical integral extensions of the housing 28, are inserted through the bottom openings 34 of the gauge housing at assembly, whereupon they are flattened into the tapered depressions which surround the openings 34, using a suitable heated tool.

The actuating lever 31 of this embodiment, being received in a recess 32 of the valve housing 28, has a shape which substantially fills out the recess. The pivot pin 40 for the actuating lever is again arranged near the forward extremity of the lever 31 which, in this case, is much narrower than the rear portion of lever 31. The orientation of the pivot pin 40 is perpendicular to the oblique mounting face for the pressure gauge 30.

Although generally triangular in contour, the actuating lever 31 has again a U-shaped cross section, the outer extremity of the valve plunger bearing against the inside of a transverse wall portion of lever 31. But, because the side walls of the actuating lever 31 are no longer parallel, the detent mechanism 36 of this embodiment is restricted to only the upper lever side wall 39 which extends in a radial plane with respect to the lever pivot axis. One of the cooperating detent members is defined by a detent groove 37 near the edge of the lever side wall 39; the other detent member is a cantilever-type spring member 38 of round spring wire. The attached end portion of the detent spring member 38 is shaped in the form of an eye portion 42, surrounding one of the two weld buttons 35 and being clamped between the valve housing 28 and the rim of the opening 34 of gauge housing 33. The free extremity of the spring member 38 is rounded to form a detent nose 41 engaging the detent groove 37 of lever 31. In this case, the detent cam formations are not triangular, but rounded, i.e. matchingly convex and concave.

The arrangement of the detent grooves 37 near the edge of the lever side wall 39 has again for its purpose to avoid frictional resistance against the movements of the actuating lever 31, until shortly before the latter reaches its fully depressed dumping position. At this point, a bevel on the edge of side wall 39 lifts the detent nose 41 onto the side wall 39. A tongue-shaped lever guide 44 extends outwardly from the bottom of the housing recess 32 with a small clearance to the inner side of the lever side wall 39, thereby serving as a support for the actuating lever 31, against the transverse bias of the detent spring member 38. A recess 43 in the upper portion of the valve housing 28 gives the detent spring member 38 freedom to move against the lever side wall 39. In the lateral sense, this recess 43 is only slightly larger than the wire diameter of the detent spring member 38, thereby positioning and guiding the latter.

In general, the operation of the deflation valve of the embodiment of FIGS. 4–6 is the same as that of the previously described embodiment, the actuating lever 31 having again an upwardly inclined release flank on its narrow forward end portion, for the application of finger pressure, when the deflation valve is to be released from the dumping position in which it is held by the detent mechanism 36. The deflation valve and pressure unit of FIGS. 4–6 is designed for right-handed operation. It should be understood that an equivalent pressure unit for left-handed operation requires only a left-to-right mirror image rearrangement of the housing recess 32, actuating lever 31, and detent mechanism 36 inside the valve housing 28.

Figure 7:
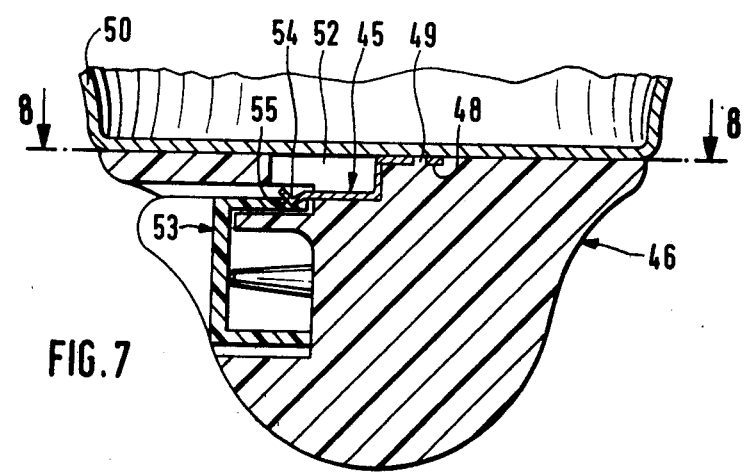
FIG. 7 shows a transverse cross section through a modified deflation valve which is similar to that of FIG. 5, taken along line 7—7 of FIG. 8.
Figure 8:
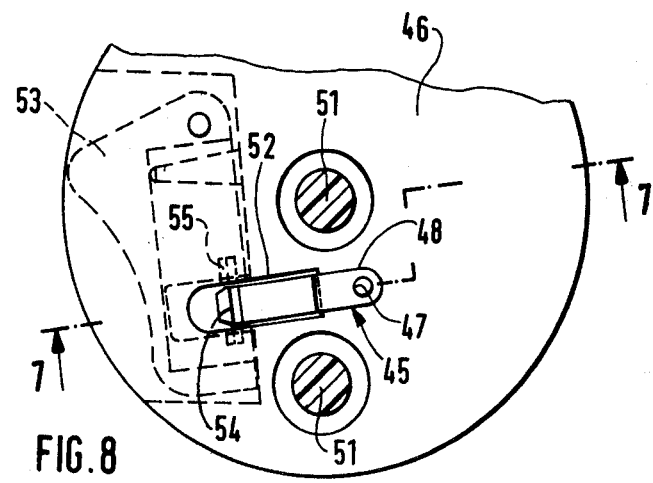
FIG. 8 shows a longitudinal cross section through the assembly of FIG. 7, taken along line 8—8 thereof.

In FIGS. 7 and 8 is shown a third embodiment of the invention which is generally similar to the embodiment of FIGS. 4–6 just described. Outwardly, the differences between these two embodiments would not be visable in FIG. 4. The device of FIGS. 7 and 8 differs from the device of FIGS. 5 and 6 only in the type of spring member which serves as the second detent member, in cooperation with the upper side wall of the actuating lever 53. The other features of this embodiment are unchanged from the previously described embodiment and will therefore not be separately described here.

Taking the place of the earlier wire spring detent member 38 is a spring member 45 of flat spring steel. This leaf spring is again of the cantilever type, having one end portion clamped between the oblique mounting face of the valve housing 46 and the bottom of the gauge housing 50. This clamped end portion of the detent spring member 45 is retained inside a shallow recess portion 48 of the valve housing 46, having a bore 47 engaged by a small integral positioning knob 49 of the valve housing 46. A downwardly offset portion of the spring member 45 is positioned inside a deep recess portion 52 of the valve housing 46, extending outwardly into the housing recess of the actuating lever 53 and engaging a detent groove 55 in the side wall of the latter.

While the detent spring member 45 is no longer positioned around one of the weld buttons 51 of the unit, its assembly is similar, though somewhat simpler, than is the case in the previously described embodiment: The detent spring member 45 is placed into its recess, the gauge housing 50 is inserted over the—initially cylindrical—weld buttons 51, and the latter are permanently set into their surrounding tapered depressions. The small positioning knob 49, engaging the bore 47 of spring member 45, prevents the latter from being pulled out of its seat in the shallow recess portion 48.

The detent cam formations of this embodiment, rather than being convexly and concavely curved, as previously, are triangular in shape, the downwardly offset length portion of the detent spring member 45 being preferably located just above the side wall of the actuating lever 53. The use of a leaf spring as a detent member has the advantage of providing a larger contact surface between the spring and the cooperating detent groove of the actuating lever, thereby greatly reducing any potential wear on the detent cam formations over the long run.

It should be understood, of course, that the foregoing disclosure describes only preferred embodiments of the invention and that it is intended to cover all changes and modifications of these examples of the invention which fall within the scope of the appended claims.

I claim the following:

1. In a manually adjustable deflation valve for the controlled release of air from a pressurizable system, such as a blood pressure measuring device, a valve actuating mechanism comprising in combination:

a block-shaped valve housing having two substantially parallel side walls, a longitudinal main axis extending centrally therebetween, and a pivot axis extending perpendicularly thereto;

an actuating lever having a generally U-shaped body profile constituted by two substantially parallel side wall portions which adjoin a central bridge wall portion and fit over the side walls of the valve housing, at least one of the three wall portions being resiliently deformable in the sense of widening the distance between the distal extremities of the side wall portions, the actuating lever being attached to the valve housing by a pivot connection in its pivot axis, in such a way that the actuating lever straddles the valve housing and its pivotability enables the lever side wall portions to execute a sweeping motion over a surface portion of the side walls of the valve housing with a small lateral clearance therebetween; and detent means defined between the valve housing and the actuating lever within said swept surface portion, for the releasable retention of the actuating lever in a pivoted end position, whereby the spring action of the detent means is provided by said resiliently deformable wall portion, or portions, of the actuating lever; and wherein:

the detent means includes duplicate detent formations in the form of detent depressions and cooperating detent protrusions on opposite sides of the valve housing and actuating lever; and the detent formations are so arranged, near the margin of said swept surface portion, that initial frictional engagement between the detent formations takes place just a minimal distance ahead of the engaged position of the detent formations.

2. A valve actuating mechanism as defined in claim 1, wherein the side wall portions of the actuating lever are thin, resiliently deformable wall portions; and the detent formations on the actuating lever are arranged at a short distance from the junctions between its bridge wall portions and its side wall portions.

3. A valve actuating mechanism as defined in claim 1, wherein the detent depressions of the detent means are in the form of detent grooves which extend at least approximately radially with respect to the pivot axis; and the detent protrusions of the detent means are in the form of cooperating matchingly oriented elongated detent ridges.

4. A valve actuating mechanism as defined in claim 3, wherein the detent grooves and detent ridges have a generally V-shaped cross-sectional profile.

5. A valve actuating mechanism as defined in claim 3, wherein the detent grooves are arranged in the side walls of the valve housing, in opposite alignment with one another; and the detent ridges are arranged on the inner sides of the side wall portions of the actuating lever.

6. A valve actuating mechanism as defined in claim 1, further comprising spring means urging the actuating lever away from the pivoted end position which is associated with the detent means, towards an oppositely pivoted rest position; and wherein the bridge wall portion of the actuating lever, in its rest position, is oriented approximately parallel to the valve housing main axis, being so related to the pivot axis that it executes an approximately radial approach movement to the valve housing main axis, when pivoted towards said detent end position, under finger pressure applied to the outer side of the bridge wall portion; and the actuating lever further includes a nose formation with a release flank adjoining the outer side of the bridge wall portion, the release flank being so oriented with respect to the pivot axis of the actuating lever that the latter pivots away from the detent end position, under finger pressure applied to the release flank.

* * * * *